United States Patent [19]

Karol et al.

[11] 4,228,008
[45] Oct. 14, 1980

[54] CHROMATOGRAPHIC DEVICE FOR SIMULTANEOUS COLLECTION AND EVAPORATION OF SEQUENTIAL VOLATILE NON-AQUEOUS ELUATES

[75] Inventors: Robert J. Karol, Andover; Raymond E. Grew, Cedar Grove, both of N.J.

[73] Assignee: Hoffmann-La Roche Inc., Nutley, N.J.

[21] Appl. No.: 27,345

[22] Filed: Apr. 5, 1979

[51] Int. Cl.³ .................................................. B01D 15/08
[52] U.S. Cl. .................................... 210/198 C; 55/197
[58] Field of Search ............ 210/31 C, 198 C; 55/68, 55/197, 386; 73/61.1 C

[56] References Cited

U.S. PATENT DOCUMENTS

| | | | |
|---|---|---|---|
| 3,427,788 | 2/1969 | Caael et al. | 55/197 |
| 3,608,276 | 9/1971 | Bloomer | 55/197 |
| 3,925,207 | 12/1975 | Scaiba | 210/198 C |
| 3,954,617 | 5/1976 | Ishimatsu | 210/198 C |
| 4,042,499 | 8/1977 | Aamstan | 210/198 C |

Primary Examiner—John Adee
Attorney, Agent, or Firm—Jon S. Saxe; George M. Gould; James H. Callwood

[57] ABSTRACT

The present disclosure relates to a chromatographic device for the simultaneous collection and evaporation of sequential volatile non-aqueous eluates. The device integrates collection and evaporation steps by continuously feeding the collected eluate directly to an evaporation vessel via a column delivery tube. As the solvent is evaporated from the evaporation vessel, eluate is continuously fed to said vessel, thereby eliminating the need for manual transfer and reducing the chances of contamination. The device increases the surface area available for evaporation, allows for the evaporation of volumes of solvent greater than the capacity of the evaporation vessel and allows for as much as a 5-fold reduction in the time necessary to carry out the chromatography and evaporation procedure.

5 Claims, 2 Drawing Figures

CHROMATOGRAPHIC DEVICE FOR SIMULTANEOUS COLLECTION AND EVAPORATION OF SEQUENTIAL VOLATILE NON-AQUEOUS ELUATES

BACKGROUND OF THE INVENTION

1. Field Of The Invention

The present invention relates to a chromatographic device for the simultaneous collection and evaporation of sequential volatile non-aqueous eluates. More particularly, the device is concerned with the integration of collection and evaporation steps by gearing the rate of collection to the rate of evaporation and increasing the surface area available for evaporation. As samples are collected, they can be continuously introduced directly to the evaporation step without the need for intermittent transfer of batches to the evaporation process.

2. Description Of The Prior Art

The ability to reliably analyze large numbers of volatile samples of chromatographic eluates has been limited by a chromatographic step which requires the collection of eluting solvent before its subsequent evaporation. This evaporation can take as much as 4-fold longer than the collection process and, in some cases, requires a transfer step involving additional glassware. This cumbersome procedure contributes to losses and possible contamination of the sample.

Typical prior art devices are characterized by Organomation's N-EVAP. Said device is comprised of a housing for a water bath in which are inserted numerous tubes containing the eluate to be evaporated. Above each tube is a nitrogen outlet connected to a manifold, which allows for the nitrogen to contact the material in each tube, thereby causing the volatile solvent to evaporate, leaving behind the sample to be analyzed.

The principle problems with the prior art devices have been the length of time necessary to carry out the collection and evaporation, the tendency of the sample to become contaminated during transfer to the evaporation medium, the availability of only a small surface area for evaporation and the inability to correlate the rate of collection with the rate of evaporation.

In accordance with the present invention, a chromatographic device for the simultaneous collection and evaporation of sequential volatile organic eluates is described wherein the collection process is integrated with the evaporation process and correlated therewith so that the collection and evaporation can be carried out in a rapid and efficient manner. Said device increases the surface area available for evaporation, eliminates contamination, allows for as much as a 5-fold reduction in the time necessary to carry out the process, allows for evaporation of and analysis of several samples from the same batch, a procedure which, in certain cases, would otherwise be too labor intensive to be practical, and allows for the evaporation of larger volumes than the volume of the evaporating vessel.

SUMMARY OF THE INVENTION

A chromatographic device for the simultaneous collection and evaporation of sequential volatile organic eluates which comprises:
a. a column for receiving sample to be separated,
b. a means for retaining said column,
c. a separating matrix disposed within said column,
d. a means for delivering eluate from said column to an evaporation vessel, said means being situated so as to allow for communication of said means with the lower end of said column,
e. a receptacle for receiving eluate, said vessel affixed in such a position to allow for communication of said vessel with the terminal end of said eluate delivery means,
f. a container for receiving eluate, said container having inlet means at several points and being positioned to allow for communication of said inlet means with the terminal end of said eluate delivery means,
g. an evaporating gas source, said source positioned to allow communication within said receptacle for receiving eluate,
h. a means for maintaining a constant temperature in which is placed said receptacle for receiving eluate,
i. a means for controlling the rate of flow of said eluate,
j. a means for supporting said device.

DETAILED DESCRIPTION OF THE INVENTION

Figure 1:
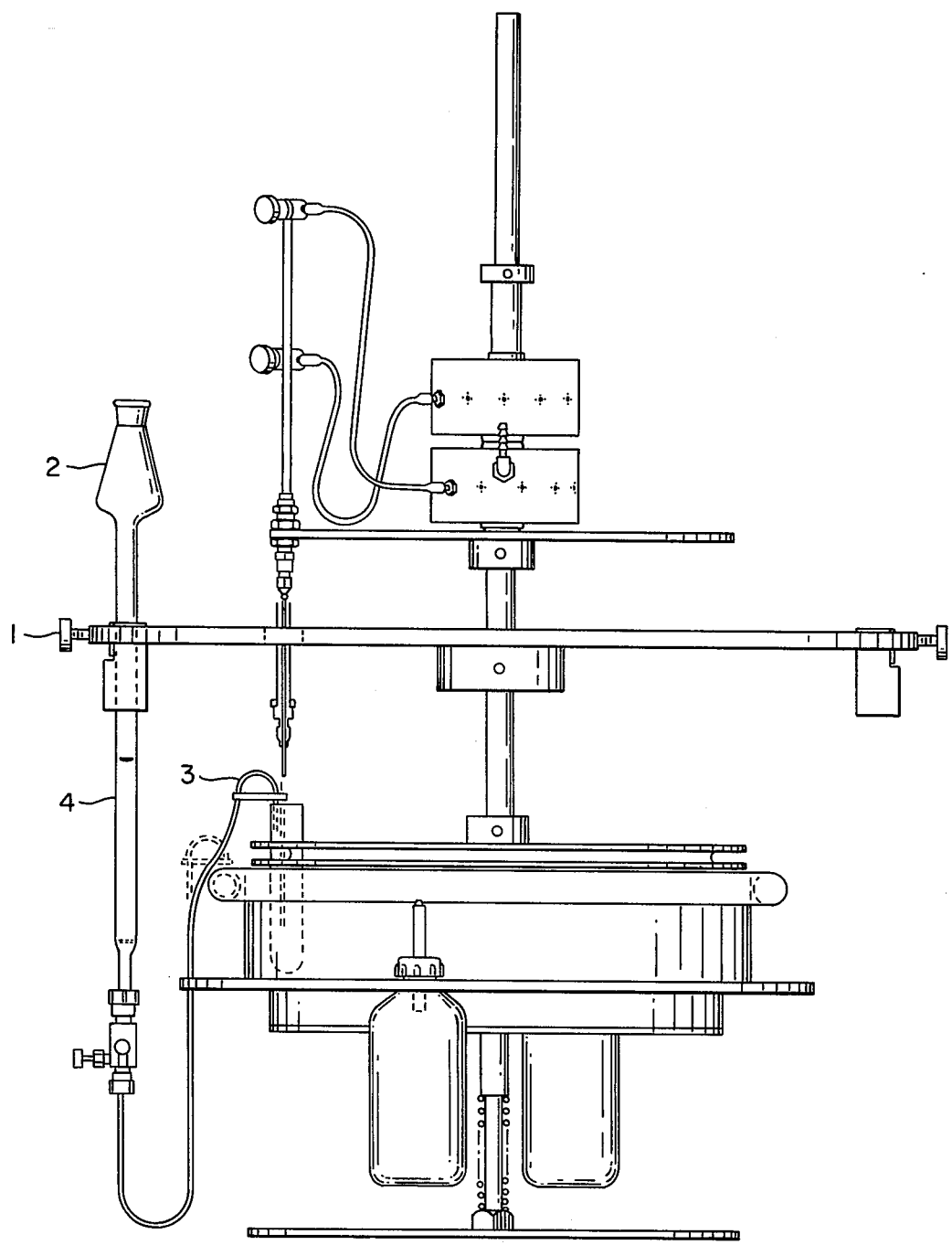
Figure 2:
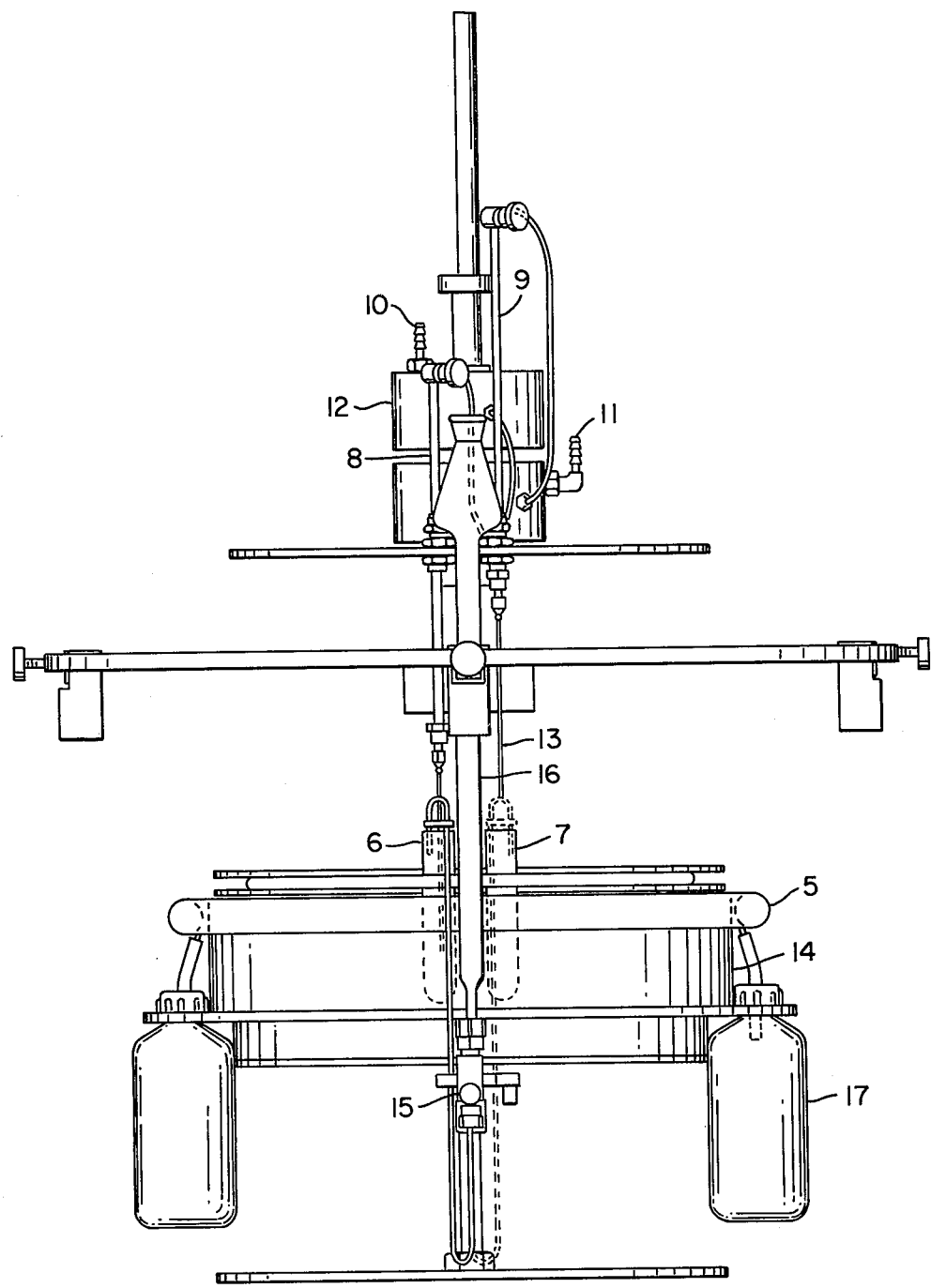

The device of the present invention can be utilized for the collection of chromatographic samples and the evaporation of any compounds requiring similar chromatographic procedures. For example, steroids are frequently separated in a similar manner. Also, the principle of collection and simultaneous evaporation of sequential column eluates could be applied to the interfacing of high-pressure liquid chromatography and mass spectroscopy by incorporating a suitably-designed fraction collecting system. For example, a train of collecting vessels would pass through the evaporating stations and then into the mass spectrophotometer.

The separating matrix may be any commercially-available chromatographic separating medium. For example, Sephadex LH-20, LH-60, Sephasorp HP, Lipidex, silica gel, alumina, etc.

The device of the present invention integrates the chromatographic separation of materials and subsequent evaporation of the eluting solvent. The disclosed design describes 12 chromatography columns coupled to a 24-position evaporator equipped with a 12-position common waste drain. However, the design of the instant device encompasses any convenient number of chromatography columns equipped with a similar number of common waste drains.

The configuration described allows for the simultaneous collection and evaporation of sequential fractions from each of 12 columns with the added advantage of processing fractions which initially have volumes larger than the collecting vessel. It is also possible to divert fractions not needing analysis to a waste container.

FIGS. I and II illustrate the design features of the device.

As is shown in FIG. I, the device has an adjustable column retaining disc (1) which accommodates 12 chromatographic columns (2) (1 shown). These columns can be adjusted vertically with respect to the highest point on the column delivery tube (3). The most advantageous operating position orients the top of the separating matrix (4) in the chromatographic column (1) slightly higher than the column delivery tube (3). This configuration reliably stops the flow of eluting solvent at the top of the separating matrix (4), thereby establishing precise volume control and preventing the separatory matrix from drying out.

Each chromatographic column is associated with a position on the waste drain (5) (see FIG. II) and two evaporating positions (6 and 7). Evaporating position 6 for columns 1-12 has a common adjustable nitrogen circuit (8). Similarly, the evaporating position (7) is associated with a nitrogen circuit (9). Each nitrogen circuit is composed of a separate nitrogen source (10 and 11), a regulator (not shown) and a nitrogen manifold (12) to evenly distribute nitrogen to the 12 evaporating positions in the circuit and is constructed to withstand operating pressures in excess of 50 PSI. Efficient evaporation is insured by a flow of nitrogen from the needle (13) of sufficient velocity to increase the surface area of the drops as they elute from the column delivery tube. The precise velocity is dependent on the physical properties of the eluting solvent, i.e., volitility, viscosity, etc. This velocity is usually attained at operating pressures greater than 20 PSI. The evaporation is also aided by a constant temperature bath (14) and a metering valve (15) which can control the rate of solvent elution.

The entire device rotates on a fixed stand (16), allowing all manipulations to be accomplished from the front.

Solvent and waste samples can be discarded by placing the column delivery tube into a position on the waste drain (5) and allowing the waste material to collect in the waste receptacle (17).

Once the fractions containing the sample are identified by analytical chromatography and the optimum operating conditions determined, i.e., flow rate of eluate and evaporation pressure and temperature, the following operation procedure can be adapted for routine analysis. Also, because the eluate is continuously being added to the evaporation tube, as the solution is evaporated, the level of eluate is replenished so that the level of eluate is always at the optimum distance from the evaporating gas needle to insure the most efficient rate of evaporation.

The samples are applied to the columns and allowed to flow into separating matrix (4). A predetermined volume of eluting solvent is then added to the columns. This volume of solvent corresponds to fraction I and, in this example, is diverted to the waste drain (5). After fraction I has eluted, the column delivery tubes are moved to the fraction collection test tubes in evaporating position (7). The nitrogen pressure in circuit 8 is adjusted as required, and the volume of solvent corresponding to fraction 2 is applied to the columns. As fraction 2 elutes from the columns, the solvent is simultaneously evaporated. After fraction 2 is completely eluted, the nitrogen pressure in circuit 8 is reduced to about 5 PSI, and a small amount of solvent is added directly to the fraction collection tubes to wash the desirable materials to the bottom where they will be gently evaporated to dryness. The column delivery tubes (3) are now moved to the test tubes in evaporating position 7, and the nitrogen pressure for circuit 9 is adjusted as required. The volume of solvent corresponding to fraction 3 is applied to the chromatographic columns and the eluting solvent simultaneously collected and evaporated, leaving behind the desired materials. The nitrogen pressure in circuit (9) is adjusted to about 5 PSI, and the desired material is washed to the bottom of the test tube and evaporated to dryness.

Any number of additional fractions could be collected and evaporated by replacing the test tubes in evaporating positions (6) and (7) and repeating the evaporation and wash steps. Also, as an alternative to evaporation, the undesired fractions could be discarded by draining into the waste drain (5) and collecting in the waste receptacle (17).

By utilizing the foregoing procedure, one operator can reliably process 24 columns simultaneously and, depending upon the time necessary for the individual chromatographic steps, multiple sets of 24 may be possible.

The foregoing procedure is adaptable for manual operation, but conversion to an automatic system could be effected using motor operators for position changes, timer, pressure regulator and manifolding for nitrogen pressure adjustments. Simultaneous column filling and washing could be accomplished using pumps, valves and piping manifolds.

In another embodiment (not shown), a venting hood for the control of noxious fumes is a functional part of the device. Since most organic solvents are toxic at some level, a fume hood is necessary to reduce exposure. Since the cost of laboratory fume hoods is high, it is proposed to confine the vapors given off during evaporation and reduce their entry to the laboratory environment by connecting the unit to an exhaust system that would draw air in radially toward the center and up across the evaporating test tubes. A sliding damper would be installed on the horizontal column support plate to adjust exhaust air quantities.

EXAMPLE I

A conventional evaporation device (Organomation's N-EVAP) was used for the evaporation process.

Serum extracts were applied to prepared Sephadex LH-20 columns in 1.5 ml of 9:1:1 solvent followed by an additional solvent wash of 1.5 ml. Seven ml was then added, and the first 10 ml were collected and discarded. An additional 18 ml was added and collected in a 25 ml volumetric flask as the 25(OH)D sample fraction. Then, another 30 ml was added and collected in a 50 ml volumetric flask as the 1,25(OH)$_2$D sample fraction.

The sample fractions were sequentially transferred to 100×16 mm disposable screw cap test tubes and evaporated to dryness under nitrogen at 37° C.

This procedure required about 12.5 hours to process 24 serum samples.

EXAMPLE II

The device of the present invention was used to carry out the evaporation under nitrogen at 37° C.

Serum extracts were applied to prepared Sephadex LH-20 columns in 1.5 ml of 90:10:10 solvent followed by an additional solvent wash of 1.5 ml. Seven ml was then added and the first 10 ml discarded. An additional 18 ml was added, collected and simultaneously evaporated as the 25(OH)D sample fraction. Then, another 30 ml was added, collected and simultaneously evaporated as the 1,25(OH)D sample fraction.

Twenty-four samples were analyzed in about 2.5 hours by this procedure.

What is claimed is:

1. A chromatographic device for the simultaneous collection and evaporation of sequential volatile organic eluates which comprises:
   a. a column for receiving sample to be separated,
   b. a means for retaining said column,
   c. a separating matrix disposed within said column, d. a column delivery tube at the lower end of said column,
e. a receptacle for receiving eluate, said vessel affixed in such a position to allow for communication of said vessel with the terminal end of said column delivery tube,
f. a container for receiving eluate, said container having inlet means at several points and being positioned to allow for communication of said inlet means with the terminal end of said column delivery tube,
g. an evaporating gas source, said source positioned to allow communication within said receptacle for receiving eluate,
h. a means for maintaining a constant temperature in which is placed said receptacle for receiving eluate,
i. a means for controlling the rate of flow of said eluate,
j. a means for housing said device.

2. The device of claim 1 wherein the means for retaining said column is an adjustable means.

3. The device of claim 2 wherein said means for delivering eluate is a tube.

4. The device of claim 3 wherein said means for maintaining a constant temperature is a water bath.

5. The device of claim 4 wherein said means for controlling flow rate is a metering valve.

* * * * *